(12) United States Patent
Saitoh et al.

(10) Patent No.: US 7,254,212 B2
(45) Date of Patent: Aug. 7, 2007

(54) PARTICULATE MATTER ANALYZER, COLLECTING FILTER AND SYSTEM FOR ANALYZING AND COLLECTING SAMPLES FROM FLUIDS

(75) Inventors: Katsumi Saitoh, Kyoto (JP); Junji Kato, Kyoto (JP); Masahiko Fujiwara, Kyoto (JP); Masayoshi Shinohara, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 10/824,881

(22) Filed: Apr. 15, 2004

(65) Prior Publication Data

US 2005/0041774 A1    Feb. 24, 2005

(30) Foreign Application Priority Data

| Apr. 16, 2003 | (JP) | 2003-112095 |
| Sep. 3, 2003 | (JP) | 2003-311765 |
| Oct. 31, 2003 | (JP) | 2003-371486 |
| Nov. 14, 2003 | (JP) | 2003-384887 |

(51) Int. Cl.
*G01N 23/223* (2006.01)
*G01N 23/225* (2006.01)
*G01T 1/36* (2006.01)

(52) U.S. Cl. ............. 378/47; 378/45; 378/49; 378/83; 250/308; 250/309; 250/310

(58) Field of Classification Search .......... 378/53, 378/45, 46, 49, 50, 83, 88, 89, 90, 47; 250/306, 250/307, 308, 309, 310
See application file for complete search history.

(56) References Cited

U.S. PATENT DOCUMENTS

| 3,744,297 A | * | 7/1973 | Hanson et al. ......... 73/865.5 |
| 4,375,718 A | * | 3/1983 | Wadsworth et al. ......... 29/886 |
| H0188 H | * | 1/1987 | Thomson et al. ......... 378/45 |
| 4,961,916 A | | 10/1990 | Lesage et al. |
| 5,317,930 A | * | 6/1994 | Wedding ......... 73/863.03 |
| 6,401,520 B1 | * | 6/2002 | Volkwein et al. ......... 73/863.22 |

FOREIGN PATENT DOCUMENTS

| DE | 31 03 176 | 8/1982 |
| DE | 38 18210 | 11/1989 |
| DE | 41 21 493 | 1/1993 |
| DE | 44 34 222 | 2/1996 |
| DE | 202 15 855 | 2/2003 |
| EP | 0 139 822 | 5/1985 |
| EP | 0 148 290 | 7/1985 |
| EP | 0 175 432 | 3/1986 |
| EP | 1 142 702 A1 | 10/2001 |
| JP | 58098112 | 6/1983 |
| JP | 05111622 | 5/1993 |
| JP | 2002239319 A | * 8/2002 |

OTHER PUBLICATIONS

Computer translation of DE 44 34 222 C1.*

* cited by examiner

*Primary Examiner*—Edward J. Glick
*Assistant Examiner*—Chih-Cheng Glen Kao

(57) ABSTRACT

A system, including a particulate matter analyzer and collecting filter, provides a method of analyzing and collecting samples from fluids, such as collecting particulate matter from air. A mass measuring unit and composition analyzing unit can be provided for either simultaneous or immediately consecutive measurements within a single instrument. The filter material can have an antistatic electricity characteristic and can be impregnated with reference material to enable calibration of the composition analyzing unit.

23 Claims, 11 Drawing Sheets

PARTICULATE MATTER ANALYZER, COLLECTING FILTER AND SYSTEM FOR ANALYZING AND COLLECTING SAMPLES FROM FLUIDS

BACKGROUND OF THE INVENTION

1. Field of the Invention

The present invention relates to an efficient measurement of particulate matter of a relatively small size and includes a particulate matter collecting filter for collecting suspended particulate matter, for example, in the atmosphere or various exhaust gases, a particulate matter analyzer for measuring the particulate matter on the collecting filter, and a system for automatically analyzing and collecting samples.

2. Description of Related Art

As one of the methods of measuring suspended particulate matter (hereinafter referred to as SPM) in the atmosphere, a predetermined flow of air from the atmosphere is continuously suctioned into a sampling tube as sample gas to continuously collect suspended particulate matter as dust on a tape filter in a vacuum chamber installed in the downstream side of the sampling tube. The collected dust is illuminated with β-rays from a β-ray source to detect the transmitted β-rays at that time through the collected dust by a detector to measure a mass of the collected dust by means of a β-ray absorption method.

In recent years, however, quantitative analysis has come to be required on not only a total amount of SPM but also on concentrations of individual components (elements). The dust collected on the filter is analyzed by various methods such as ion chromatography, fluorescent X-ray analysis or PIXY (charged particle induced X-ray analytical method) to thereby analyze concentrations of individual components contained in the dust quantitatively. To analyze SPM on not only a total weight (mass or concentration) but also individual components contained in SPM as described above, it is important in specifying a source of SPM to secure a meaningful sample.

In a case where SPM in the dust is quantitatively analyzed on individual components thereof, for example, by means of an ion chromatographic instrument, a fluorescent X-ray analyzer or a PIXY analyzer, it has been necessary to use a complicated procedure such as preparation of a calibration curve for a known specimen and to provide a sensitivity correction in an instrument described above before a quantitative analysis can be made on each component of the SPM.

With regard to suspended particulate matter which exits in the atmosphere, SPM having a diameter of 10 mm or less has been found to especially impair human health, while SPM having a diameter of 2.5 mm or less, which is referred to as micro particulate matter or PM2.5, is reported to have a close relationship with a higher human death rate.

As one of the techniques of measuring the mass (concentration) of the SPM in the atmosphere, for example, there is a method using a manually-operated sampler such as a low volume sampler. Specifically, the sampler is configured to collect the SPM on a filter by drawing a predetermined flow rate of the atmosphere continuously into a sampling tube for obtaining a sample gas and, then, making the sample gas pass through the filter provided in a downstream side of the sampling tube. The SPM is collected on the filter in this sampler for over a day to a few days and, after that, the mass of the particles is measured by means of a balance or the like, so that the concentration of the SPM can be determined from the mass of the collected SPM and the flow rate of the sample gas. See, for example, Japanese Unexamined Patent Publication No. 2001-343319).

With regard to a material for the filter, a fluororesin, which has a superior chemical stability and a low hygroscopicity, is mainly used. However, a filter made of a fluororesin is generally sensitive to electrification, so that such a filter has a disadvantage to absorb also unwanted matter together with the collected particulate matter due to such electrification. The absorption of the unwanted matter due to the electrification occurs during the collecting of particulate matter with the sampler, and in particular, such absorption occurs remarkably during the measurement of the mass on the collected filter which has been transferred from the sampler to a balance. This is a cause of a large measurement error in the analysis of the particulate matter.

In recent years, there has been an increasing demand for more specific composition analysis of the SPM. Therefore, a filter on which the SPM has been collected can be analyzed by means of an X-ray spectrometer for determining the composition of the SPM. See, for example, Japanese Unexamined Patent Publication No. 10-68684 (1998).

However, the above conventional method can be very time-consuming because the mass measurement of the SPM by means of a balance and the composition analysis of the SPM by means of an X-ray spectrometer are carried out separately.

Alternatively, another technique of measuring the mass of the SPM collected from the atmosphere utilizes a so-called β-ray absorption method wherein the mass of the filter on which the SPM has been collected is not measured by means of a balance, but a measuring spot formed by collecting particulate matter on a filter is irradiated with β-rays and the mass of the SPM is measured on the basis of the detection value of the transmitted rays.

However, since the filter used in the β-ray absorption method is usually made of a glass fiber containing silicon, sodium, zinc and the like which comparatively absorb X-rays, it has been difficult for the X-ray spectrometer to carry out a composition analysis of the SPM collected on the filter.

SUMMARY OF THE INVENTION

The present invention is made in consideration of the above circumstances, and it is an object thereof to provide a particulate matter collecting filter capable of collecting the particulate matter appropriately, and a particulate matter collecting sampler using the same.

In order to achieve the above object, a particulate matter collecting filter includes a porous layer made of a fluororesin, and an air-permeable reinforcing layer which is provided on one surface of the porous layer, wherein the reinforcing layer is made of a porous resin material having a low electrification characteristic. Specifically, the reinforcing layer is made of a non-woven fabric which consists of, for example, any one or a plurality of materials selected from polyethylene, polyethylenetelephtalate, nylon, polyester and polyamide. The filter should be made of a material other than the measuring target material to prevent the possibility of error. Additionally, the reinforcing layer can have a tag or reference material added in a known amount to act as a reference during a measurement cycle.

Further, a particulate matter collecting sampler includes a filter holding mechanism which holds a plurality of filters which are detachable respectively, and a sample gas supplying mechanism which passes the sample gas into one of the filters held by the filter holding mechanism and collects the particulate matter contained in the sample gas on the filter and the sample gas supplying mechanism collects the particulate matter successively on the plurality of filters held in the filter holding mechanism.

Specifically, the filter holding mechanism can be a turntable which is rotatable around an axis thereof, wherein the respective filters are mounted detachably on a circumference of the turntable. As an alternative filter, a roll of filter material can be advanced through a measurement zone.

A fluororesin which is made into the porous layer is generally sensitive to electrification. However, the reinforcing layer has an antistatic characteristic (destaticizing effect), so that the reinforcing layer prevents effectively the porous layer from any electrification which would cause the absorption of unwanted matter in the atmosphere. Thus, the particulate collecting filter according to the invention represents an improvement in accuracy of the measurement of the collected particulate matter.

Further, a conventional filter made of a fluororesin is usually held by a support ring made of another type of resin and is disposed around the filter made of the fluororesin in order to save weight. The whole porous layer of the present invention is made of a fluororesin and is supported by the reinforcing layer, so that a reduction in thickness and weight can be achieved.

Still further, the particulate collecting filter permits a highly sensitive quantitative analysis of the particulate matter, and moreover, such analysis can be practiced continuously and easily. Further, the plurality of particulate matter collecting filters can be readily detached from the turntable one by one.

It is an object of the present invention to provide a particulate matter analyzer and a method capable of measuring the mass or the concentration of particulate matter in a sample gas taken from the atmosphere and the like and, also, capable of analyzing the composition of the particulate matter easily and certainly.

In order to achieve the above object, a particulate matter analyzer according to the invention includes a collecting unit for collecting particulate matter in a sample gas, a mass measuring unit for measuring the mass of the particulate matter, and a composition analyzing unit for analyzing the composition of the particulate matter collected by means of the collecting unit.

Specifically, the composition analyzing unit is configured to analyze the composition of the particulate matter by means of irradiating the measuring spot formed on the filter with radioactive rays such as X-rays or electron beams.

Preferably, the collecting unit is configured to allow the sample gas to pass through the filter, thereby forming a measuring spot on the filter, and the filter is made of a material which minimizes the absorption of X-rays.

Further, the mass measuring unit may be configured to measure the mass of the particulate matter by using any one or a combination of a plurality of methods such as a β-ray absorption method, a pressure loss method and a light scattering method.

According to the invention, the analyzer includes the mass measuring unit and the composition analyzing unit; therefore, the mass and concentration measurement for the particulate matter contained in the sample gas taken from the atmosphere or the like and the composition analysis for the particulate matter can be executed simultaneously or successively. In addition, there is no need to carry out the mass and concentration measurement and the composition analysis for the particulate matter by making use of different devices, only a small space is required for setting the whole device, and further, the time or labor consumed for transferring the collected particulate matter from the mass measuring device to the composition analyzing device can be saved. As a result, it becomes easy to automate the mass and concentration measurement as well as provide calibration for a composition analysis for the particulate matter.

According to the invention, a known X-ray spectrometer or a PIXY analyzer, for example, can be used for the composition analyzing unit without modification and, moreover, the particulate matter collected on the measuring spot can be analyzed non-destructively.

According to the invention, a filter made of materials that will minimize the absorption of X-rays enables the X-ray composition analysis to be executed easily and certainly.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details.

Figure 1:
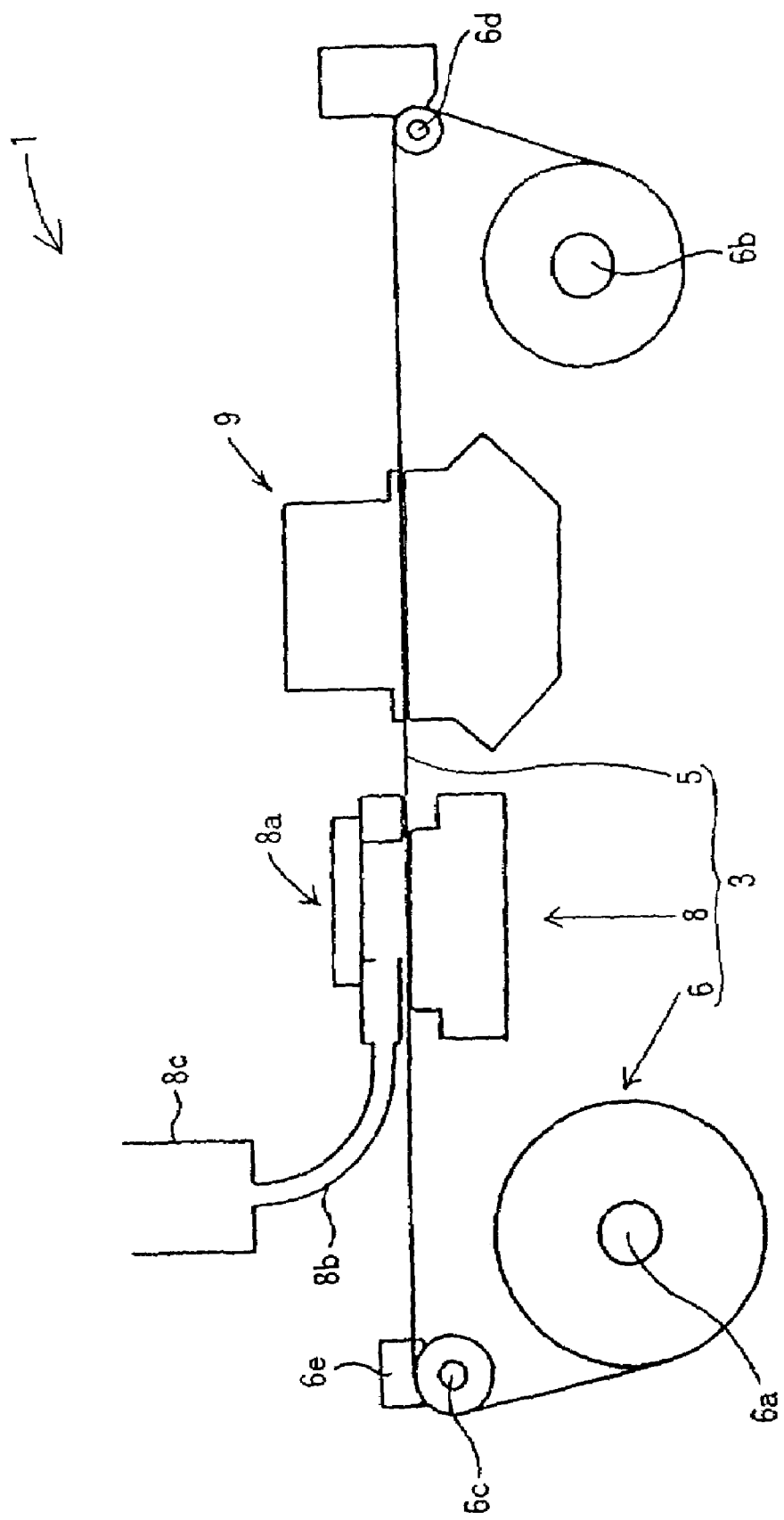
FIG. 1 schematically illustrates the configuration of a particulate matter analyzer according to a first embodiment of the invention.
Figure 2:
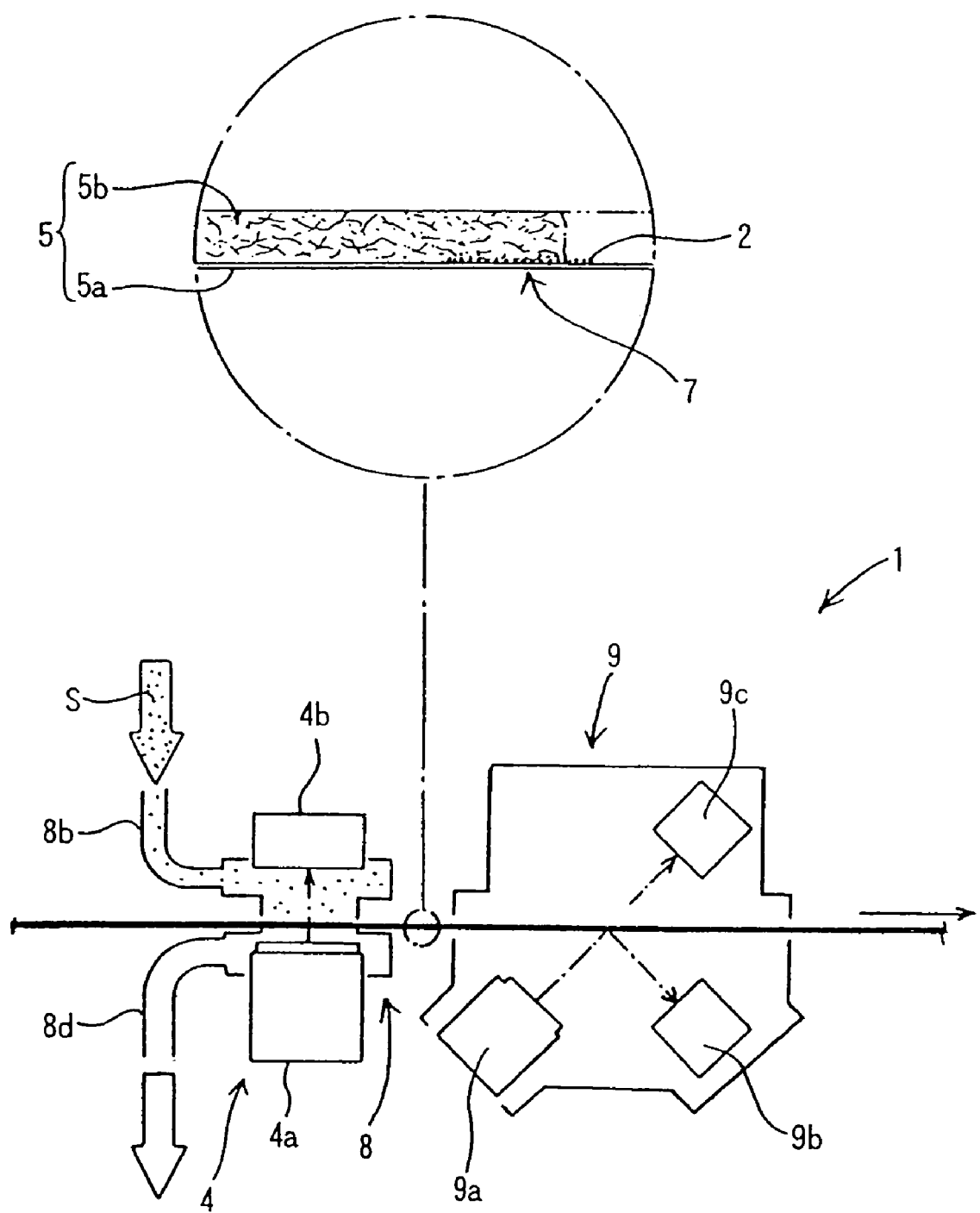
FIG. 2 schematically illustrates the configuration of a main part in the first embodiment.

FIGS. 1 and 2 show a first embodiment of the invention, respectively.

A particulate matter analyzer (hereinafter, referred to as an analyzer) 1 according to this embodiment is suitable for analyzing, for example, SPM in the atmosphere, particularly, fine particulate matter such as PM2.5. As shown in FIGS. 1 and 2, the analyzer 1 includes a collecting unit 3 which collects particulate matter (SPM) 2 contained in the atmosphere as a sample gas S, and a mass measuring unit 4 which measures the mass of the SPM 2.

The collecting unit 3 includes a tape-shaped filter 5, a filter holding mechanism 6 which holds the tape-shaped filter 5, and a sample gas supplying mechanism 8 which makes the sample gas pass through a part of the tape-shaped filter 5 held by the filter holding mechanism 6 to collect the SPM 2 contained in the sample gas 5 on the tape-shaped filter 5, thereby forming a measuring spot 7.

Hereinafter, description will be given of the constituent elements of the collecting unit 3.

The tape-shaped filter 5 has a laminated structure of a porous layer 5a and a reinforcing layer 5b as shown in FIG. 2 in an enlarged scale, and is made of materials which hardly absorb X-rays. Specifically, the porous layer 5a is formed of a porous film made of a fluororesin (e.g., tetrafluoroethylene resin) which is mainly composed of fluorine, carbon and hydrogen which hardly absorb X-rays. On the other hand, the reinforcing layer 5b is formed of a non-woven fabric with low hygroscopicity which is made of any of polyethylene, polyethylenetelephtalate, nylon, polyester or polyamide. Additionally, the reinforcing layer 5b can have an antistatic characteristic. The porous layer 5a and the reinforcing layer 5b are combined together in an appropriate manner such as adhering or sewing. It is noted that the tape-shaped filter 5 can be about 40 meters in length and 4 cm in width and provided on a roll. The reinforcing layer 5b must have sufficient strength to be pulled from a dispensing roll to a storing reel.

Herein, the porous layer 5a of the tape-shaped filter 5 is set to have a thickness of 80 to 90 mm. In addition, the weight of the porous layer 5a is set in a range from 0.1 to 1 mg/cm$^2$. In this embodiment, the weight is set to about 0.3 mg/cm$^2$. On the other hand, the weight of the reinforcing layer 5b is set in a range from 1.0 to 2.0 mg/cm$^2$. In this embodiment, the weight is set to about 1.2 mg/cm$^2$.

The thickness of the tape-shaped filter 5 is set to be in a range from 100 to 200 μm as an average value. In this embodiment, the thickness is set to about 140 μm. In addition, the weight of the tape-shaped filter 5 is set in a range from 1.0 to 3.0 mg/cm$^2$ as an average value. In this embodiment, the weight is set to about 1.5 mg/cm$^2$.

The filter holding mechanism 6 has a feeding reel 6a around which the tape-shaped filter 5 is wound in a roll and a winding reel 6b which winds up the tape-shaped filter 5 fed from the feeding reel 6a, and is configured to feed a predetermined length of the tape-shaped filter 5 in a predetermined time periodically (for example, in every 1 hour). The tape-shaped filter 5 after being fed from the feeding reel 6a and before being wound up into the winding reel 6b is held with an appropriate tension by two reels 6c and 6d. Further, the reel 6c is provided with a transfer sensor 6e which detects if a predetermined length of the tape-shaped filter 5 is fed from the feeding reel 6a to the winding reel 6b.

The sample fluid or gas supplying mechanism or unit 8 has, as shown in FIG. 1, a chamber 8a which is configured to permit the tape-shaped filter 5 traveling therethrough, a sample gas introducing pipe 8b which supplies a predetermined flow rate of the atmosphere as the sample gas S into the chamber 8a, a size separator 8c which is provided in an upstream side of the sample gas introducing pipe 8b, and a sample gas discharge pipe 8d (see FIG. 2) which discharges the sample gas S introduced into the chamber 8a to outside. In addition, a sampling pump (not shown) such as a vacuum pump is provided at, for example, an appropriate position of the sample gas discharge pipe 8d.

The size separator 8c is configured to classify the size of the particulate matter 2 (SPM) contained in the atmosphere S, collect the large-size particulate matter 2 which has a diameter larger than a predetermined value and supply selectively only the small-size particulate matter 2 which has the diameter smaller than a predetermined value via the sample gas introducing pipe 8b toward the chamber 8a.

It is noted that, in regard to the size separator 8c, a cyclone-type separator (generally called cyclone) which classifies particles on the basis of centrifugal separation in a vortex flow of the sample gas S, or an impact-type separator (generally called impactor) which collects selectively only the small particulate matter 2 by making use of an impingement effect inside the sample gas S can be used.

The mass measuring unit 4 can be configured to measure the mass and concentration of the particulate matter 2 collected in the measuring spot 7 on the tape-shaped filter 5 employing a β-ray absorption method. As shown in FIG. 2, the mass measuring unit includes a β-ray source 4a which irradiates the measuring spot 7 formed on the tape-shaped filter 5 with β-rays from one side (lower side) of the measuring spot 7, and a β-ray detector 4b which is placed in the other side (upper side) of the measuring spot 7 and detects β-rays transmitted through the measuring spot 7. Further, the β-ray detector 4b is provided with a proportional counter which outputs signals depending on the intensity of the detected β-rays. The mass measuring unit 4 is configured to determine the mass of the particulate matter 2 by processing appropriately the outputs of the detection from the β-ray detector 4b and also determine the concentration of the particulate matter 2 from the mass and the flow rate of the sample gas S supplied to the chamber 8a by the sample gas supplying mechanism 8.

It is noted that the β-ray source 4a is received in the chamber 8a of the sample gas supplying mechanism 8 so as to be positioned directly below the measuring spot 7 formed by the collecting unit 3, and that the β-ray detector 4a is received in the chamber 8a so as to be positioned directly above and opposite to the β-ray source 4a with respect to the measuring spot 7.

The composition analyzing unit 9 is arranged in a downstream side with respect to the chamber 8 in the traveling direction of the tape-shaped filter 5, whereby the composition (for example, the metallic elements) in the particulate matter 2 collected by the collecting unit 3 can be analyzed. The composition analyzing unit 9 includes an X-ray spectrometer which irradiates the measuring spot 7 formed on the tape-shaped filter 5 with X-rays so as to analyze the composition such as the metallic elements of the particulate matter 2. It is noted that examples of the X-ray spectrometer may include an energy dispersive X-ray spectrometer, a total reflection X-ray fluorescence spectrometer and the like.

Specifically, the composition analyzing unit 9 includes an X-ray source 9a which irradiates the measuring spot 7 with a flux of X-rays (primary X-rays) having a predetermined diameter from one side (lower side) thereof, a fluorescent X-ray detector 9b which consists of, for example, a semiconductor detector for detecting the fluorescent X-rays excited from the measuring spot 7 by the primary X-rays emitted from the X-ray source 9a, and a transmitted X-rays detector 9c which is placed on the other side (upper side) of the measuring spot 7 and adapted to detect the primary X-rays transmitted through the measuring spot 7 so as to output signals depending on the intensity of the transmitted X-rays. The composition analyzing unit 9 is configured to appropriately process the outputs from the fluorescent X-ray detector 9b and the transmitted X-ray detector 9c, thereby analyzing the composition such as the metallic elements of the particulate matter 2. The operation of the analyzer 1 having the above configuration will be described later.

The tape-shaped filter 5 before absorbing (collecting) particulate matter 2 is wound in a roll around the feeding reel 6a, for example, by a motor (not shown), and is fed from the feeding reel 6a with a predetermined length in every predetermined period of time (1 hour) to effectively provide a plurality of filter segments or members that are sequentially transported for measurement of mass and composition. The particulate matter 2 is collected onto the tape-shaped filter 5, which has been fed as described above, in the chamber 8a, so that a measuring spot 7 is formed. Then, the particulate matter 2 collected in the measuring spot 7 is subjected to a measurement with the mass measuring unit 4 and, subsequently, to an analysis with the composition analyzing unit 9. Then, the tape-shaped filter 5 which has finished the measurement and analysis is successively wound around the winding reel 6b.

Specifically, the analyzer 1 according to this embodiment starts the operation in winding up the tape-shaped filter 5 by the winding reel 6b. When the transfer sensor 6e detects that a predetermined length of the tape-shaped filter 5 is fed from the feeding reel 6a side toward the winding reel 6b side, the winding up of the tape-shaped filter 5 by the winding reel 6b is stopped by the sensor. Thus, the tape-shaped filter 5, which is fed intermittently from the feeding reel 6a as described above, travels through the reel 6c, the chamber 8a, the composition analyzing unit 9 and reel 6d in this order, and is wound around the winding reel 6b.

Then, the atmosphere sample S is introduced into the size separator 8c by the suction effect of the sampling pump provided in the downstream side of the chamber 8a.

The atmosphere S, from which the particulate matter 2 having the diameter beyond the desired measuring object is excluded with the assistance of the size separator 8c, is caused to flow through the sample gas introducing pipe 8b into the chamber 8a. Subsequently, the atmosphere S is caused to pass through a part of the tape-shaped filter 5 fixed inside the chamber 8a from the upper side to the lower side of the filter, and to discharge through the sample gas discharge pipe 8d to the outside of the chamber 8a. During this process, the atmosphere S is kept in the state of passing through the tape-shaped filter 5 for a predetermined period of time (1 hour in this embodiment), so that the measuring spot 7 is formed.

In concurrence with the formation of the measuring spot 7, the mass measuring unit 4 is operated to measure the particulate matter 2 collected in the measuring spot 7. The measurement with the mass measuring unit 4 comprises the steps of irradiating the measuring spot 7 with β-rays from the β-ray source 4a and detecting the transmitted β-rays with the β-ray detector 4b so as to obtain the intensity of β-rays transmitted through the measuring spot 7. Then, the mass and concentration of the particulate matter 2 to be measured can be derived from the measured intensity by a calculation using a known predetermined formulae which can be pre-stored in a computer. That is to say, the mass and concentration of the particulate matter 2 can be measured not only after the measuring spot 7 is completed but also during the formation of the measuring spot 7.

When the step of forming the measuring spot 7 and the step of measuring the mass thereof with the mass measuring unit 4 are completed, the winding reel 6b restarts to winding up the tape-shaped filter 5. The measuring spot 7 which has been measured with the mass measuring unit 4 is forwarded to the composition analyzing unit 9 for the analysis with the composition analyzing unit 9. The analysis with this composition analyzing unit 9 comprises the steps of irradiating the measuring spot 7 with X-rays from the X-ray source 9a and detecting the primary and the transmitted X-rays with the fluorescent X-ray detector 9b and the transmitted X-ray detector 9c. Then, the composition such as the metallic elements of the objective particulate matter 2 can be derived by processing appropriately the detection outputs from the respective detectors 9b and 9c again by a pre-stored known algorithm in a computer.

Subsequently, the part of the tape-shaped filter 5, which has been subjected to the analysis with the composition analyzing unit 9, including the measuring spot 7, travels through the reel 6d and is finally wound around the winding reel 6b, and is stored in this state for future reference purposes.

The various measurements such as the amount of air sampled and the detector measurement signals can be automatically supplied to a computation device such as a microcomputer or microcontroller to control both the operation and to calculate the measurement results in response to a known measurement algorithm.

According to an analyzer 1 having the above-described configuration, the measurement of the mass and concentration and the analysis of the composition such as the metallic elements for the particulate matter 2 collected on the tape-shaped filter 5 can be executed automatically and continuously without special requirements such as cutting of the tape-shaped filter 5.

Further, since a filter used for a conventional analyzer is made of a glass fiber which absorbs X-rays relatively well and contains a number of metallic elements such as aluminum, silicon, lead and zinc, the composition analysis with an X-ray spectrometer can be unsuccessful for such a conventional analyzer. On the contrary, since the tape-shaped filter 5 according to this embodiment is made of materials which are less likely to absorb X-rays and contains an extremely little amount of metallic elements except titanium which is used as a colorant (white) for a non-woven fabric consisting of the reinforcing layer 5b, the composition analyzing unit 9 including an X-ray spectrometer can be extremely improved in the accuracy of the analysis for the composition. As a consequence, the analyzer 1 enables not only the qualitative analysis but also the quantitative analysis for the metallic elements of the particulate matter 2.

Further, the non-woven fabric included in the reinforcing layer 5b of the tape-shaped filter has an antistatic characteristic to counter the effect of the fluororesin included in the porous layer 5a of the tape-shaped filter 5, which is easily affected by static electricity. Accordingly, the measuring spot 7 formed on the tape-shaped filter 5 is prevented from any unnecessary absorption of dust during traveling from the chamber 8a toward the composition analyzing unit 9 due to an electrical charge. As a consequence, the analyzer 1 is enabled to make an analysis with an extremely high accuracy.

Figure 3:
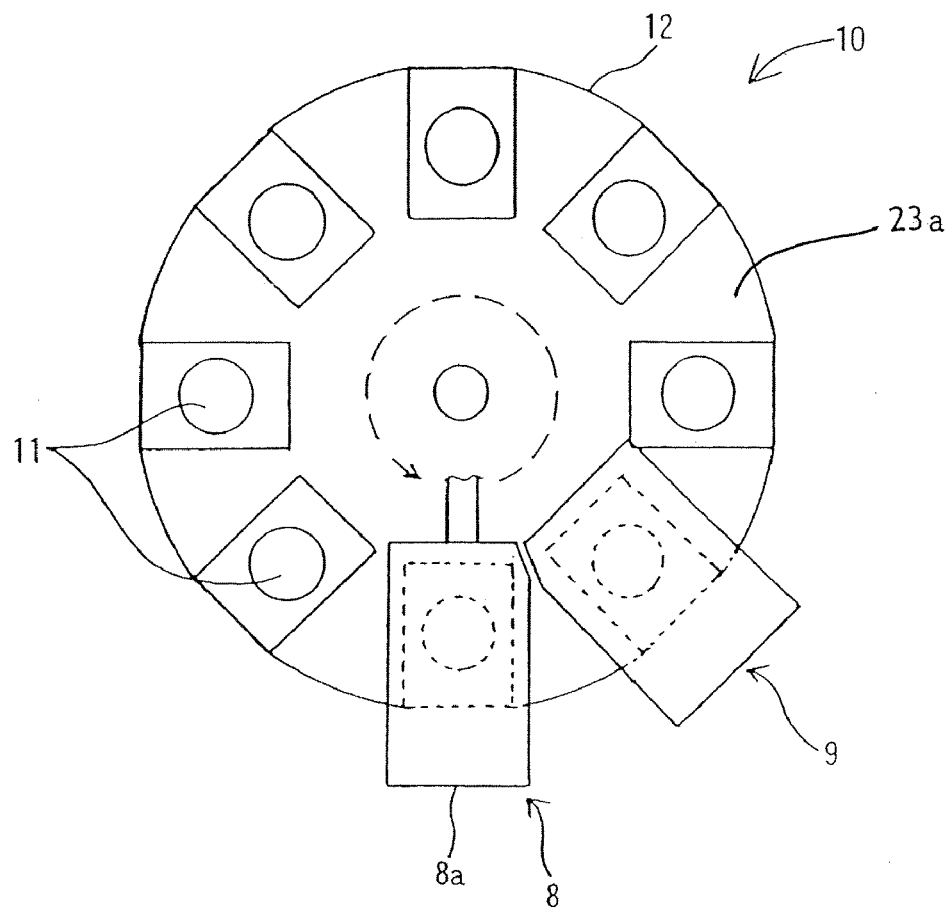
FIG. 3 is a plan view schematically showing the configuration of a particulate matter analyzer according to a second embodiment of the invention.
Figure 4:
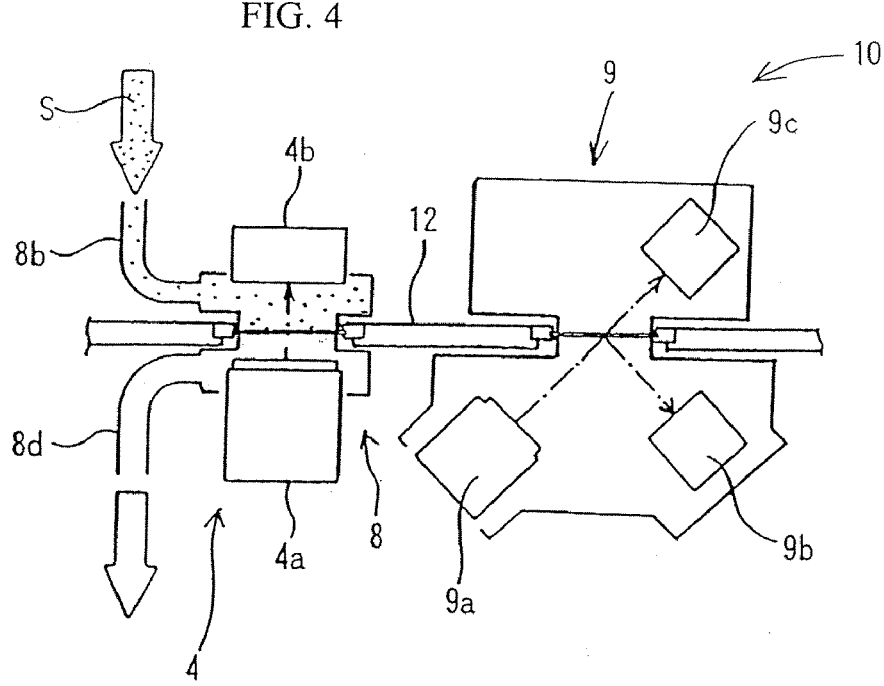
FIG. 4 schematically illustrates the configuration of a main part in the second embodiment.

FIGS. 3 and 4 show a second embodiment according to the invention. It is noted that the same structural members illustrated in the first embodiment will be given to same reference numerals in the second embodiment; therefore, a description thereof will not be repeated.

In comparison of the analyzer 10 according to the second embodiment to that of the analyzer 1 according to the first embodiment, these two analyzers are similar in that they have the collecting unit 3 which collects the particulate matter 2 contained in the atmosphere as the sample gas S, the mass measuring unit 4 which measures the mass of the particulate matter 2, and the composition analyzing unit 9 which analyze the composition such as the metallic elements in the particulate matter 2. However, the analyzer 10 is different from the analyzer 1 in that the analyzer 10 is provided with a plurality of filters 11 instead of the tape-shaped filter 5 of the analyzer 1 and a filter holding mechanism 12 of a turntable-type structure 23a for holding the plurality of filters 11 instead of the filter holding mechanism 6 of the analyzer 1 for holding the tape-shaped filter 5.

Specifically, the collecting unit 3 in this embodiment includes the plurality of filters 11, the filter holding mechanism 12 which holds all of the filters 11, and a sample gas supplying mechanism 8 which allows the sample gas S to pass through the filters 11 held by the filter holding mechanism 12 so as to collect the particulate matter 2 in the sample gas S onto the filters 11, thereby forming the measuring spots 7.

The filters 11 are, as shown in FIG. 3, in substantially a circular shape in a plan view. Besides, the filters 11 are of no difference from the tape-shaped filter 5 in the first embodiment in that the filters 11 have a double layer structure consisting of the porous layers 5a and the reinforcing layers 5b and that the filters 11 are made of the materials which absorb less X-rays.

On the other hand, the filter holding mechanism 12 has a turntable which detachably holds the plurality of filters 11 (for example, 8 filters in FIG. 3) which are spaced by an equal distance on the circumference thereof.

The sample gas supplying mechanism 8 according to this embodiment has a chamber 8a in which a circumference of the filter holding mechanism 12 having the turntable travels therethrough and is configured not to prevent the rotation of the filter holding mechanism 12, a sample gas introducing pipe 8b which supplies a predetermined flow rate of the atmosphere as the sample gas S into the chamber 8a, a size separator 8c (not shown) provided in an upstream side of the sample gas introducing pipe 8b, and a sample gas discharge pipe 8d which discharges the sample gas S to the outside of the chamber 8a. Moreover, a sampling pump such as a vacuum pump (not shown) is provided in an appropriate portion of the sample gas introducing pipe 8d.

Further, the chamber 8a is configured to be positioned over only a single filter 11 among the plurality of filters 11 which are held in the periphery of the filter holding mechanism 12, and the composition analyzing unit 9 is configured to be positioned over the filter next to the same covered by the chamber 8a.

It is noted that another configuration of the analyzer 10 according to the second embodiment is the same as that of the analyzer 1 according to the first embodiment; therefore, a description thereof will not be repeated.

Now, the operation of the analyzer 10 having the above-described configuration will be described.

The filter holding mechanism 12, in which the plurality of filters 11 are mounted on the circumference thereof, is rotated by a predetermined angle (45° in this embodiment) in a predetermined period of time (1 hour) around a vertical axis, and collects the particulate matter 2 on one of the filters 11 having entered into the chamber 8a so as to form the measuring spot 7 on the filter. Then, the particulate matter 2 collected in the measuring spot 7 is subjected to a measurement with the mass measuring unit 4 received in the chamber 8a and an analysis with the composition analyzer which is arranged next to the chamber 8a. Then, the inspected filter 11 is detached (recovered) from the filter holding mechanism 12 for storage, and the next filter 11 is attached to the position where the inspected filter has been detached therefrom.

Specifically, with respect to the analyzer 10 according to this embodiment, at first, the filter holding mechanism 12 is rotated for 45° around the vertical axis in a predetermined direction (counterclockwise in FIG. 3), then stopped.

Subsequently, the atmosphere S is introduced into the size separator 8c by the suction of the sampling pump provided in the downstream side of the chamber 8a. The atmosphere S, from which particulate matter 2 having a larger diameter, out of a measuring range is excluded with the assistance of the size separator 8c, is caused to flow through the sample gas introducing pipe 8b into the chamber 8a. Then, the atmosphere S is caused to pass through the filter 11 positioned in the chamber 8a from the upper side of the filter to the lower side of the same, and discharged from the sample gas discharge pipe 8d to the outside of the chamber 8a. During this process, the atmosphere S is kept in the state of passing through the filter 11 for a predetermined period of time (1 hour), so that the measuring spot 7 is formed.

In concurrence with the formation of the measuring spot 7, the mass measuring unit 4 is operated to measure the particulate matter 2 collected in the measuring spot 7. The details of the measuring process by means of the mass measuring unit 4 is the same as those described with respect to the first embodiment.

After forming the measuring spot 7 and performing the mass measurement with the mass measuring unit 4, the filter holding mechanism 12 is rotated again around the vertical axis for the predetermined angle (45°) and stopped. In this manner, the filter 11 which has completed the measurement with the mass measuring unit 4 is transferred to the composition analyzing unit 9 for analyzing the composition with the composition analyzing unit 9. The details of the analyzing process are the same as those described with respect to the first embodiment.

Then, the filter 11 which has completed an analysis with the composition analyzing unit 9 is finally detached from the filter holding mechanism 12, and stored in an appropriate state.

It is noted that the present invention is not limited to the above embodiments, and various modifications may be available. For example, the sample gas is not limited to the atmosphere, but may be exhaust gases such as engine emission gases or flue gases, or diluted exhaust gases generated by diluting the exhaust gases. In these cases, particulate matter 2 to be analyzed is the particulate matter contained in these exhaust gases.

Further, the mass measuring unit 1 is not limited to a type based on the β-ray absorption method. For example, other procedures could be used such as a pressure loss method or a light scattering method can be used instead of the β-ray absorption method, or an appropriate combination of any two or three from those of β-ray absorption, pressure loss and light scattering methods can be arranged for measuring the mass and concentration of the particulate matter 2.

For example, in the case of the light scattering method, optical windows are formed oppositely on an annular side wall of the sample gas introducing pipe 8b, and a light source, which emits the infrared light, for example, is provided at the outside of one of the optical windows and a scattered light detector (light sensor) is provided at the outside of the other optical window.

When the infrared light is emitted into the atmosphere S flowing through the sample gas introducing pipe 8b, the scattered light is generated from the particulate matter 2 contained in the atmosphere S. Therefore, the mass measuring unit 4 can be arranged to detect the intensity of the light scattered from the particulate matter 2 which has a diameter smaller than a predetermined value.

Further, the composition analyzing unit 9 can be arranged to analyze a composition such as the metallic composition in the particulate matter 2 by detecting the characteristic X-rays generated by irradiating radiation beams such as electron beams other than X-rays.

Further, the period of time of passing the sample gas S through the tape-shaped filter 5 or the filter 11 for collecting the particulate matter 2 contained in the sample gas S is generally set for 1 hour. However, it can be desirable to extend this period of time suitably, for example, from a few hours to a few days in order to improve the analyzing accuracy of the composition analyzing unit 9.

Figure 5:
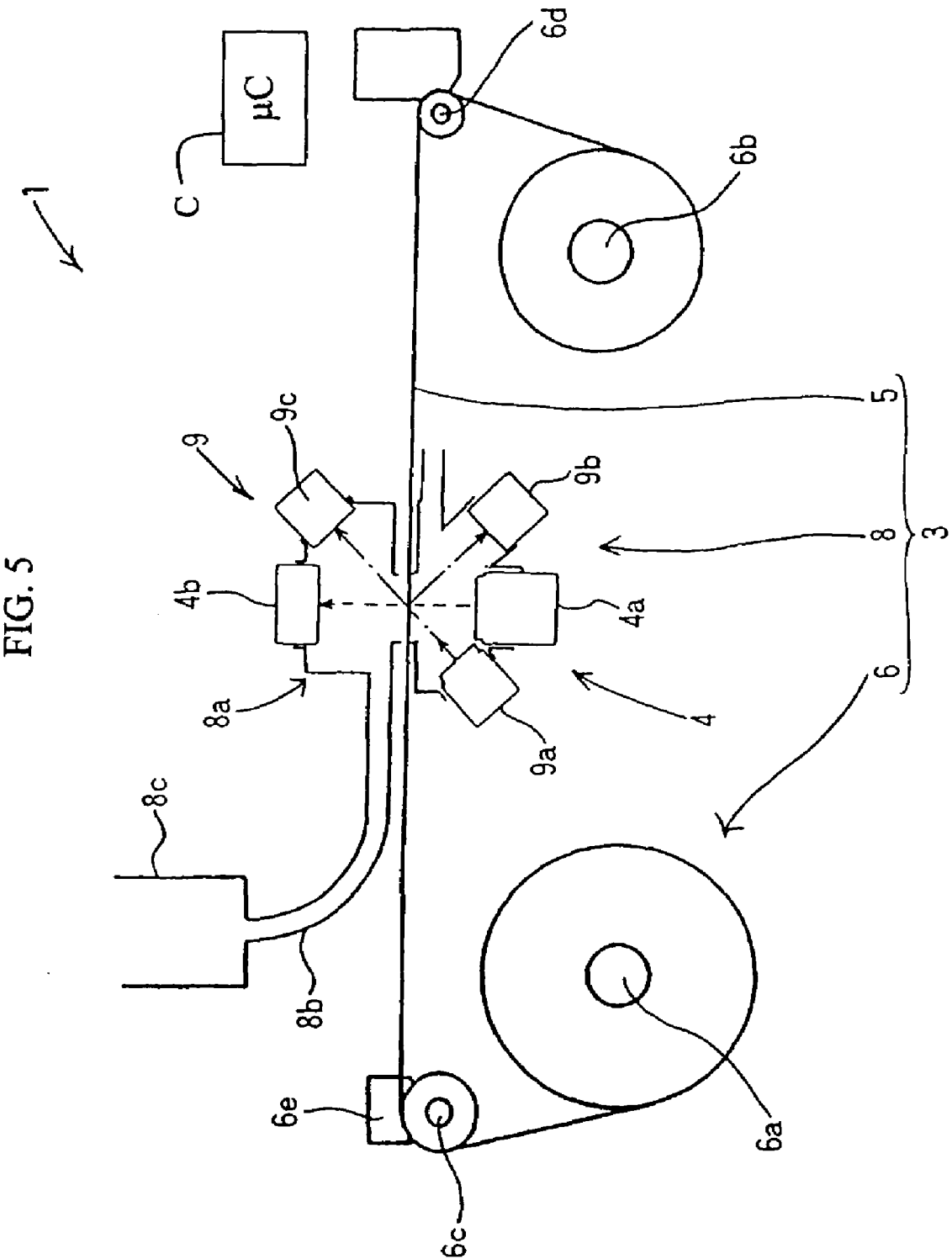
FIG. 5 schematically illustrates the configuration of a modification of the first embodiment.

In addition, the analyzer 1 according to the first embodiment is not limited to a type which includes the chamber 8a, the mass measuring unit 4 and the composition analyzing unit 9 separately. For example, as shown in FIG. 5, not only the β-ray source 4a and β-ray detector 4b, but also the X-ray source 9a, the fluorescent X-ray detector 9b and the transmitted X-ray detector 9c are provided in the same chamber or housing, so that the chamber 8a, the mass measuring unit 4 and the composition analyzing unit 9 can be configured integrally. Advantageously, the analyzer 1 is permitted to become compact in this manner. Also, the analyzer 10 according to the second embodiment can be designed in the same manner.

A controller C such as a microcomputer, shown in FIG. 5, can automatically coordinate a series of measurements with a plurality of filter members, and measurements of mass and composition can be performed within the same housing. When the filter member includes a predetermined reference material other than a target material to be collected, it is possible to initially calibrate the composition analyzing unit 9 before measuring for the target material by comparing the measurement of the predetermined reference material with a stored value and providing a compensation value if necessary.

Further, the respective embodiments show the arrangement having both the fluorescent X-ray detector 9b and the transmitted X-ray detector 9c. However, the invention is not limited to this type of arrangement. That is, for example, the composition analysis may be carried out with any one of the fluorescent X-ray detector 9c and the transmitted X-ray detector 9c.

Figure 6A:
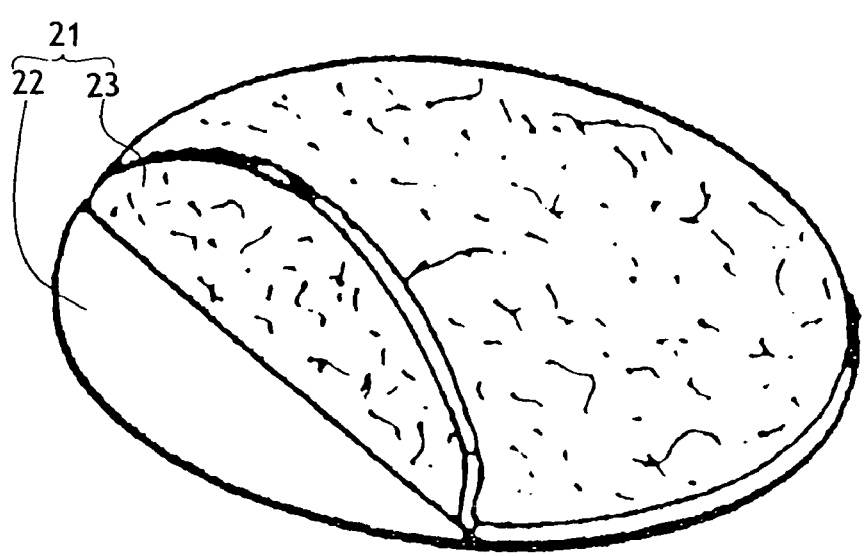
FIGS. 6A and 6B are an illustration and a vertical sectional view, each schematically showing a configuration of a particulate collecting filter.
Figure 6B:
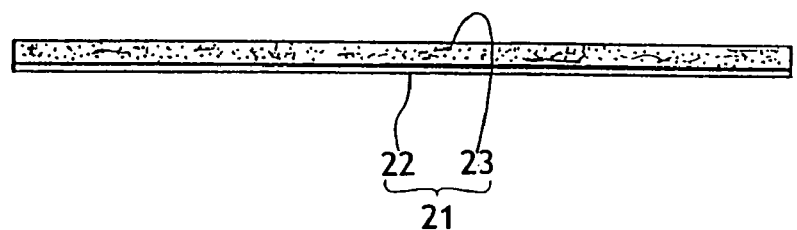

FIGS. 6A and 6B show a particulate matter collecting filter (hereinafter, simply referred to as a filter) according to another embodiment of the invention. This filter 21 is used for collecting the particulate matter contained in a sample gas. For example, the filter is suitable for collecting SPM in the atmosphere, particularly, fine particulate matter such as PM2.5. This filter 21 has the shape of, for example, a circle in a plan view, and has a multiple layer structure (two-layer structure) including a porous layer 22 as a filter body made of a fluororesin and a reinforcing layer 23 which is air permeable and provided on one of the surfaces of the porous layer 22 (lower side in the figure), wherein the reinforcing layer 23 is made of a porous resin material which has a low electrification characteristic.

Specifically, the porous layer 22 includes a porous film made of a fluororesin such as a tetrafluoroethyleneresin. The reinforcing layer 23 includes a non-woven fabric which is made of any one or a plurality of materials selected from polyethylene, polyethylenephtalate, nylon, polyester and polyamide and has a low hygroscopic property. These porous layer 22 and reinforcing layer 23 are combined together with an appropriate method such as sticking.

More specifically, the porous layer 22 of the filter 21 has a thickness of 80 to 90 mm, for example. The weight of the porous layer 22 is preferably in a range from 0.1 to 1 mg/cm$^2$. In this embodiment, the weight is set to about 0.3 mg/cm$^2$. On the other hand, the weight of the reinforcing layer 23 is preferably in a range from 1.0 to 2.0 mg/cm$^2$. In this embodiment, this weight is set to about 1.2 mg/cm$^2$.

Further, the whole thickness of the filter 21 is preferably in a range from 100 to 200 mm as an average value. In this embodiment, the thickness is set to be about 140 mm. Still further, the weight of the filter 21 is preferably in a range from 1.0 to 3.0 mg/cm$^2$ as an average value. In this embodiment, the weight is set to be about 1.5 mg/cm$^2$.

Figure 7:
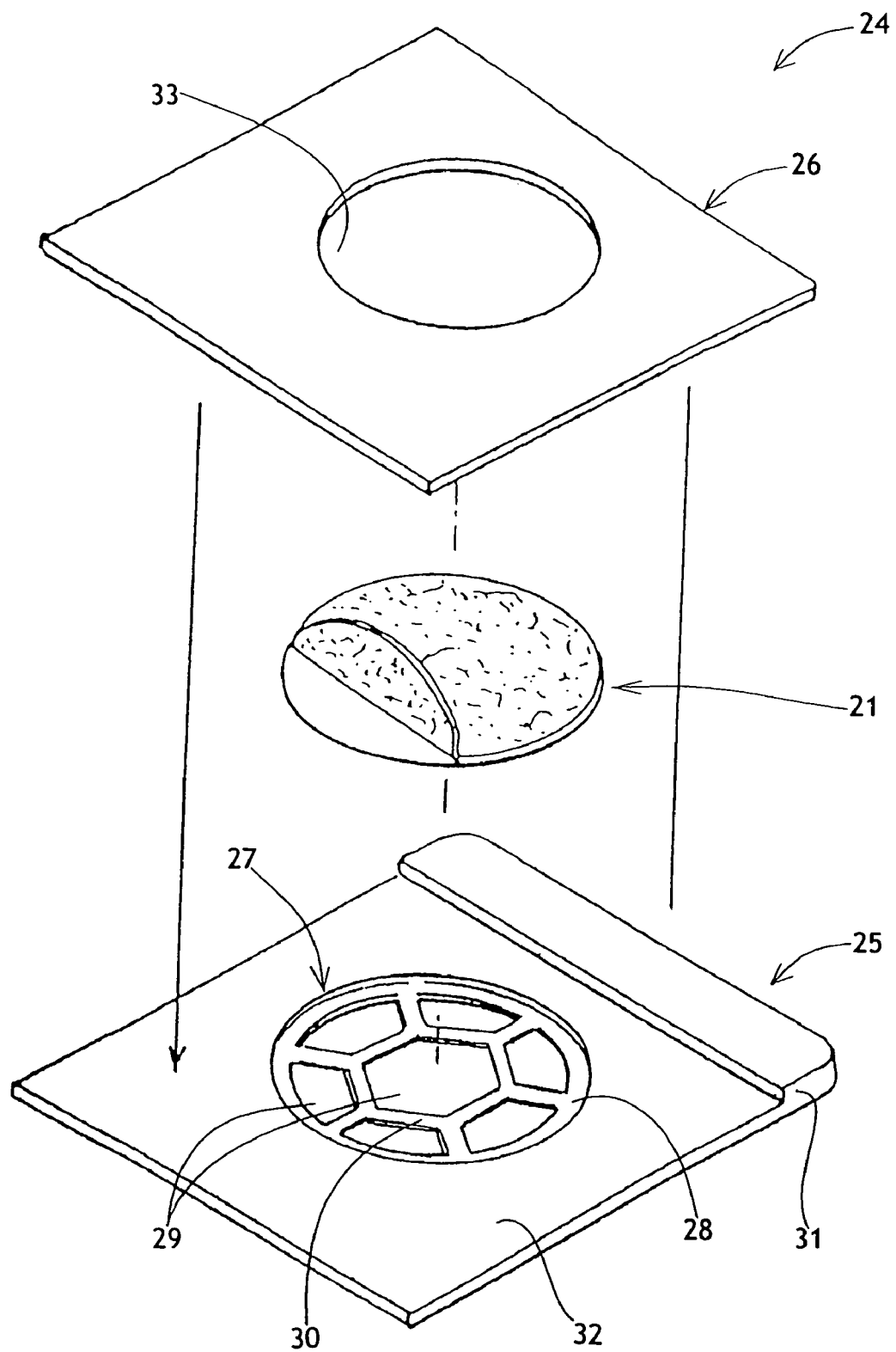
FIG. 7 is a perspective view schematically showing the configuration of a filter unit which is assembled with the filter.

FIG. 7 shows an example of a filter unit 24 in which the filter 21 is assembled. This filter unit 24 is configured to hold the filter 21 between a base plate 25 and a retaining plate 26 and to allow the sample gas to pass through the filter 21 held therebetween. This filter unit 24 is placed, for example, in a flow passage (not shown) of the sample gas.

Specifically, the base plate 25 is a plate having substantially a rectangle shape in a plan view, and formed with a center portion which is lowered by a step from the surrounding environment. This center portion serves as a filter mounting part 27 to which filter 21 is mounted. The filter mounting part 27 has an annular portion 28 which is formed on the inner periphery thereof and adapted to abut against the outer periphery of the filter 21, and a plurality of through-holes 29 and a plurality of bridges 30 which are formed in the center portion thereof, the through holes serving to pass the sample gas therethrough, and the bridges, which have an appropriate shape, abutting against the filter 21 from the downstream side (lower side in the figure) of the filter and serving to prevent the filter 21 from being deformed toward the downstream side and broken by the flow of the sample gas.

In addition, the base plate 25 comprises a thick plate portion 31 and a mounting face portion 32, wherein the thick plate portion 31 is formed on an end of one of the surfaces (top surface) of the base plate 25 with a top surface which is raised from the remaining portion of this top surface with the height corresponding to the thickness of the retaining plate 26, and the remaining portion of this top surface except the thick plate portion 31 serves as the mounting face portion 32 for receiving the retaining plate 26. Note that the mounting face portion 32 and the retaining plate 26 are formed to have substantially the same shape and dimension. Thus, when the retaining plate 26 is placed over the mounting face portion 32, the top surface of the retaining plate 26 becomes substantially even with the top surface of the thick plate portion 31.

Figure 10:
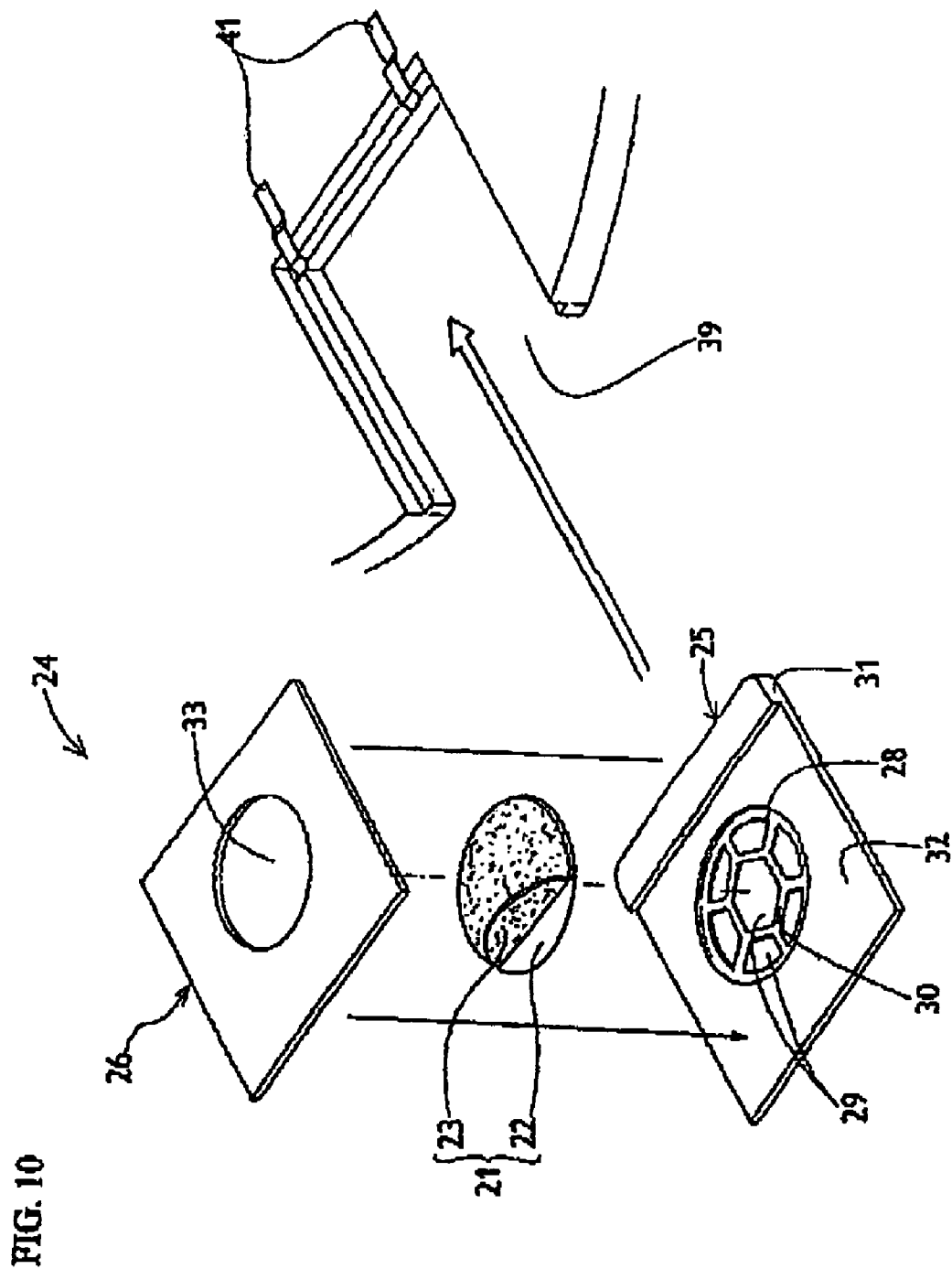
FIG. 10 is a perspective view schematically showing the configuration of a mounting portion in the sampler.
Figure 11:
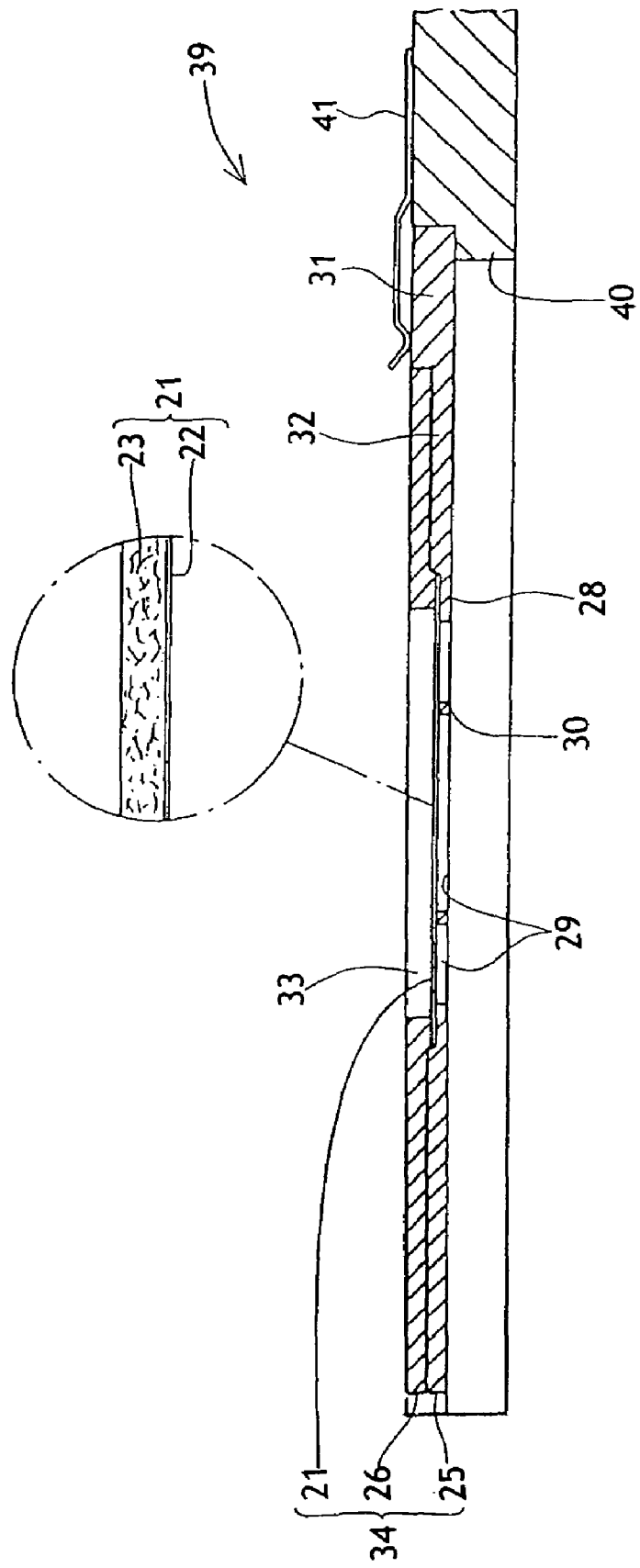
FIG. 11 is a vertical sectional view schematically showing the configuration of the mounting portion.

On the other hand, the retaining plate 26 is a plate having the shape of substantially a rectangle in a plan view, and formed with a through hole 33 at substantially the center thereof, which through hole 33 has the shape of a circle as same as that of the filter 21 in a plan view and has the diameter slightly smaller than that of the filter 21. Accordingly, the center of the filter mounting part 27 of the base plate 25 is adapted to coincide automatically with the center of the through hole 33 of the retaining plate 26, when the retaining plate 26 is placed over the mounting face portion 32 of the base plate 25 as shown in FIG. 10. Thus, when the filter 21 is placed into the filter mounting part 27 of the base plate 25 and the retaining plate 26 is placed over the mounting face portion 32, thereby fixing the filter 21 between the base plate 25 and the retaining plate 26, the periphery of the filter 21 comes to be held between the portions adjacent to the annular portion of the base plate 25 and the periphery of the through hole 33 of the retaining plate 26, respectively.

Figure 8:
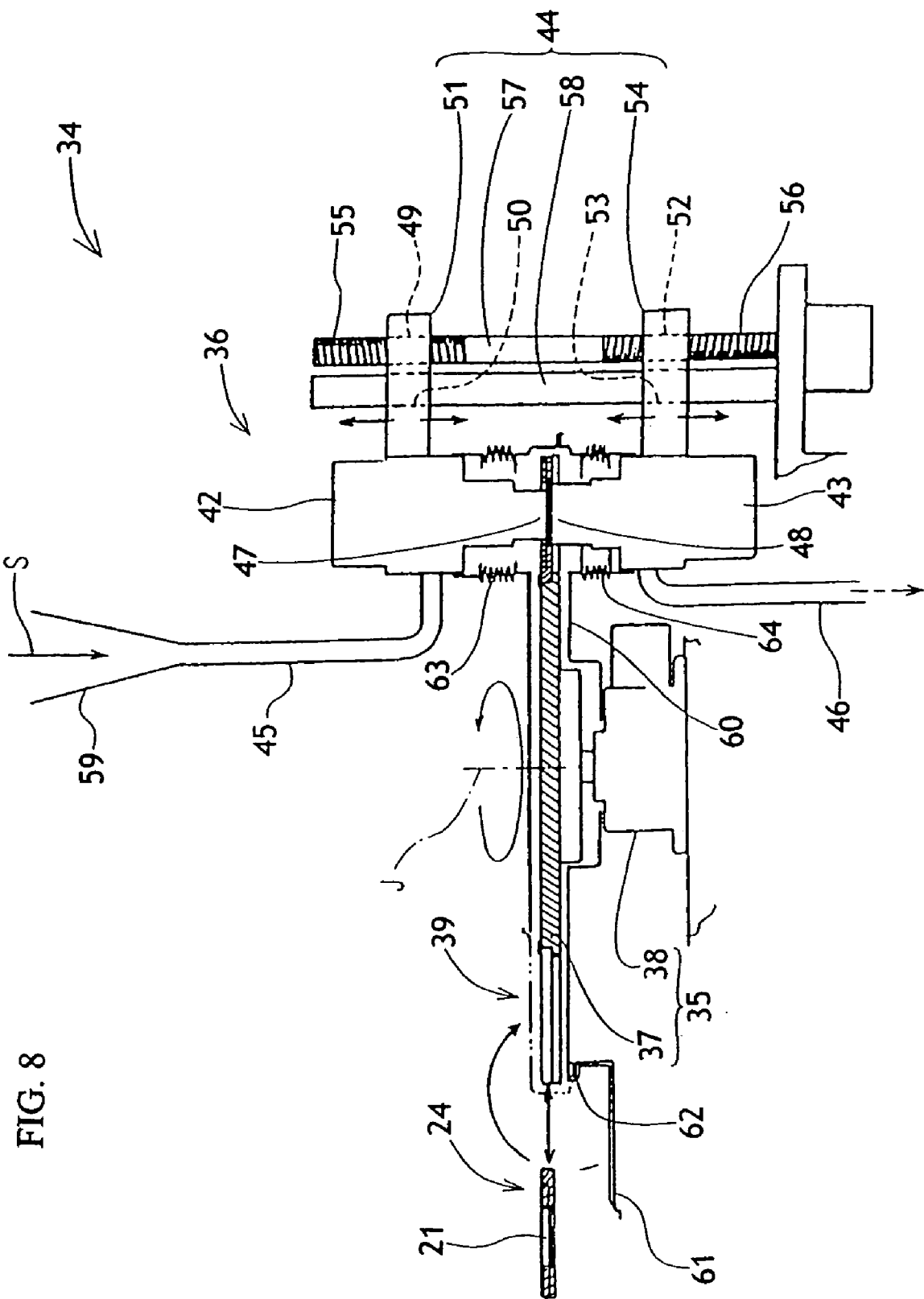
FIG. 8 schematically illustrates the configuration of a particulate matter sampler using the filter unit.

FIG. 8 shows a particulate matter sampler 34 (hereinafter, simply referred to as a sampler) attaching the filter units 24 thereto for collecting the particulate matter. This sampler 34 can be used for collecting the particulate matter contained in the sample gas S, and is suitable for collecting the SPM, especially the fine particulate matter such as PM2.5, in the atmosphere.

The sampler 24 includes a filter holding mechanism 35 and a sample gas supplying mechanism 36, the filter holding mechanism 35 holding a plurality of the filter units 24 which are detachable respectively and retain the filters 21 between the base plate 25 and the retaining plate 26, and the sample gas supplying mechanism 36 passing the sample gas through one of the plurality of filter units 34 to collect the particulate matter contained in the sample gas onto the filter 21 held in this filter unit 34, whereby the sample gas supplying mechanism 36 is configured to collect the particulate matter on the filters 21 in a plurality of the filter units 34 held in the filter holding mechanism 35 successively.

Figure 9:
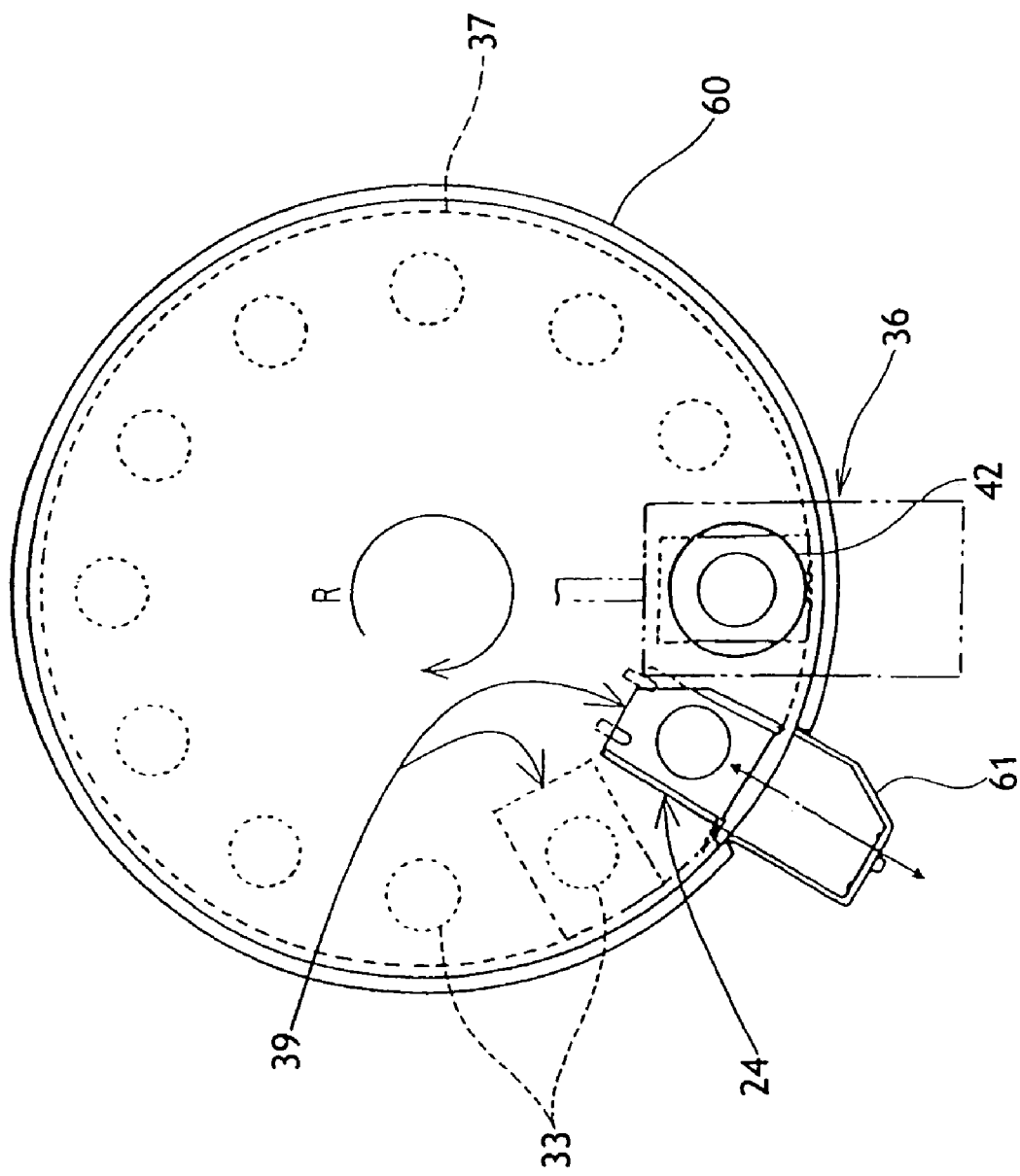
FIG. 9 is a plan view schematically showing the configuration of a main part of the sampler.

The filter holding mechanism 35 includes, as shown in FIGS. 8 and 9, a turntable 37 rotatable around its vertical center axis J and a driving unit 38 including a motor or the like for rotating the turntable 37, wherein a plurality of the filter unit mounting bays 39 (12 bays in the figured example), which filter units 34 are detachably mounted therein and are provided on the circumference of the turntable 37.

As shown in FIG. 9, the turntable 37 is driven by the driving unit 38 in a predetermined direction R (clockwise, for example) at a predetermined angle in an appropriate period of time, namely, intermittently. According to this embodiment, it is set to rotate 30° in every 24 hours.

The plurality of filter unit mounting bays 39 are spaced with an equal distance along the circumference of the turntable 37, and each one of the filter unit mounting bays 39 is, as shown in FIG. 10, cut off from the circumference of the turntable 37 toward the center thereof with an appropriate length, and the cut portions have the shape of a rectangle in a plan view.

Further, the filter unit mounting bay 39 is provided with a protruded portion 40, protruding toward the inside, on the lower edge of the perimeter of the filter unit mounting bay 39, so that the perimeter of the filter unit 24 comes to be held by the protruded portion 40 when the filter unit 24 is inserted into the filter unit mounting bay 39 from the outside thereof toward the inside.

In addition, the filter unit mounting bay 39 is provided with a plurality of spring members 41. As shown in FIG. 10, respective spring members 41 abut against the top surface of the filter unit 24 which is held above the protruded portion 40 and biases the filter unit 24 downward, so that the spring members 41 can serve to prevent the filter unit 24 from being displaced from the filter unit mounting bay 39.

The sample gas supplying mechanism 36 has an upper chamber 42, a lower chamber 43, a displacing unit 44, a sample gas introducing pipe 45 and a sample gas outlet pipe 46, the upper chamber 42 being placed above the filter unit mounting bay 39 which is provided on the circumference of the turntable 37, the lower chamber 43 being placed opposite to the upper chamber 42 with respect to the mounting portion 25, the displacing unit 44 supporting the two chambers 42, 43 and moving the two chambers 42, 43 in the direction of separating or approaching each other, the sample gas introducing pipe 45 supplying the sample gas into the upper chamber 42, and the sample outlet tube 46 discharging the sample gas transferred into the lower chamber 43 to the outside. A sampling pump (not shown) such as a vacuum pump is installed at an appropriate position in the sample gas outlet tube 46. The sampling pump is controlled to suck the atmosphere using a mass flow controller (not shown), a differential pressure method or the like, so that the sucking flow rate can be set to meet the specified flow rate, i.e., 16.7 l/min.

The upper chamber 42 is provided with a sample gas delivery port 47 in the lower end thereof, which delivery port 47 abuts against the top surface of the retaining plate 26 to cover the through hole 33 of the retaining plate 26 holding the filter 21 and serves to deliver the sample gas S flown through the sample gas introducing pipe 45 onto the top surface of the filter 21. The lower chamber 43 is provided with a sample gas receiving port 48 in the upper end thereof, the receiving pot 48 abuts against the bottom surface of the base plate 25 to cover all of the through holes 29 (or the filter mounting part 27) of the base plate 25 holding the filter 21 and serves to receive the sample gas which passes through the filter 21 from its top surface to its bottom surface.

The displacing unit 44 includes, as shown in FIG. 8, an upper chamber arm 51, a lower chamber arm 54, a rod type member 57 and a guide bar 58, the upper chamber arm 51 supporting the upper chamber 42 and having a female screw 49 and a guide hole 50 which are disposed vertically, the lower chamber arm 54 supporting the lower chamber 43 and having a female screw 52 and a guide hole 53 which are disposed vertically, the rod type member 57 penetrating through the female screws 49, 52, being threaded with male screws 55, 56 which mate with the female screws 49, 52 and being rotatable around its own vertical axis, and the guide bar 58 penetrating through the guide holes 50, 53. Note that the female screw 49, 52 are threaded oppositely to each other, and accordingly, the male screws 55, 56 of the rod type member 57 are also threaded oppositely to each other.

With respect to the displacing unit 44 configured as described above, when the rod type member 57 is rotated in one direction, the upper chamber arm 51 having the female screw 49 which mates with the male screw 55 of the rod type member 57 is caused to displace upward with the guide of the guide bar 58, and the lower chamber arm 54 having the female screw 52 which mates with the male screw 56 of the rod type member 57 is caused to displace downward with the guide of the guide bar 58. As a result of such displacement, the upper chamber 42 supported by the upper chamber arm 51 is displaced upward, and the lower chamber 43 supported by the lower chamber arm 54 is displaced downward, whereby the two chambers 42, 43 are caused to be displaced away from each other.

To the contrary, when the rod type member 57 is rotated in the other direction the upper chamber arm 51 is caused to be displaced downward with the guide of the guide bar 58, and the lower chamber arm 54 is displaced upward with the guide of the guide bar 58. As a result of such displacement, the upper chamber 42 is caused to displace downward and the lower chamber 43 is caused to displace upward, and these two chambers 42, 43 approach each other, and finally the upper chamber 42 and the lower chamber 43 come to hold therebetween the filter unit 24 which is inserted with the filter 21.

Note that a size separator 59 is disposed in the upstream portion of the sample gas introducing pipe 45. The size separator 59 is arranged to classify the SPM, PM2.5 and PM10 contained in the atmosphere, to trap the particulate matter having the diameter larger than a predetermined value, and to supply selectively the fine particulate matter having the diameter smaller than a predetermined value to the upper chamber 42 via the sample gas introducing pipe 45.

As the size separator 59, by way of exemplification, there is a cyclone which classifies the particle size by the centrifugal separation in the vortex flow of the sample gas or an impactor which take samples of the particulate matter with the small diameter selectively making use of an impingement effect inside the sample gas S.

The sampler 34 is, as shown in FIGS. 8 and 9, provided with a cover 60 which covers the turntable 37 entirely. The cover 60 separates the filter units 24 held in the turntable 37 from the outside of the cover 60, so that the cover 60 serves to prevent the filter 21 inserted in the filter unit 24 from contacting with the outside (air) of the cover 60. Also, the cover 60 has the shape substantially similar to the exterior of the turntable 37 and is structured not to impede the turntable 37 rotating around its axis.

Further, the cover 60 is provided on its circumference with a lid 61 which is operable for open and close, which lid 61 is pivotable around a hinge 62 disposed on the bottom surface of the cover 60. When the lid 61 is in the closed position, the inside of the cover 60 is kept off the air from the outside of the cover 60. When the lid 61 is in the open position, the filter unit 24 can be attached/detached to/from the filter unit mounting portion 25.

Still further, the cover 60 is structured to cover not only the turntable 37 but also a lower side wall of the upper chamber 42 and a upper side wall of the lower chamber 43, the lower side wall including also the periphery of the sample gas delivery port 47, and the upper side wall including also the periphery of the sample gas receiving port 48. In order to assist the vertical displacement of the upper chamber 42 and the lower chamber 43, there are provided bellows 63, 64, which are stretchable vertically, in the portions of the cover 61 covering the lower side wall of the upper chamber 42 and the upper side wall of the lower chamber 43.

Yet further, the sampler 34 is configured to hold one of a plurality of the filter unit mounting bays 39 provided on the circumference of the turntable 37 between the upper chamber 42 and the lower chamber 43 of the sample gas supplying mechanism 46. The lid 61 of the cover 60 is disposed in a position engaging the filter unit mounting bay 39, which position is next to the filter unit mounting bay 39 held between the upper and lower chambers 42, 43 and located in the downstream side of the direction of rotation of the turntable 37.

Now, the operation of the sampler 34 having the above configuration will be described.

A filter unit 24 is mounted into a filter unit mounting bay 39 of the sampler 34 beforehand. At first, as shown in FIG. 9, the lid 61 of the cover 60 is opened, then a filter unit 24 is inserted into one of the filter unit mounting bays 39, which is positioned to engage the lid 61, from the side thereof. Then, the turntable 37 is rotated so that all of the filter unit mounting bays 39 are moved successively into the position engaging the lid 61 and mounted with the filter units 24. In this manner, the respective filter unit mounting bays 39 are mounted with the filter units 24. After the completion of mounting the filter units 24, the lid 61 is closed.

Next, the upper chamber 42 and the lower chamber 43, which have been separated from each other, are made to displace by the operation of the displacing unit 44, and come to hold one of the filter units which is positioned for engaging the sample gas supplying mechanism 36.

Subsequently, the atmosphere S is absorbed and led into the size separator 59 with the aid of a sampling pump which is provided in the downstream side of the lower chamber 43, and the atmosphere S, which has removed particulate matter by the size separator 59, enters into the upper chamber 42 via the sample gas introducing pipe 45. Then, the atmosphere S is delivered through the sample gas delivery port 47 of the upper chamber 42, made to pass through the filter 21, which is held in the filter unit 24 fixed between the upper chamber 42 and the lower chamber 43, from the upper surface thereof to the lower surface thereof, and is discharged to the outside from the lower chamber 43 through the sample gas outlet pipe 46. The atmosphere S passes through the filter 21 for a predetermined period of time (24 hours in this embodiment), and thus the collection of the particulate matter on the filter 21 is completed.

When the collection of the particulate matter on the filter 21 is completed as described above, the turntable 37 is rotated 30°. As the turntable is rotated, the filter unit 24 including the filter 21, which is completed to collect the particulate matter thereon by means of the sample gas supplying mechanism 36, is moved to the position engaging the lid 61 of the cover 60.

Then, the lid 61 is opened, and the filter unit 24, which includes the filter 21 with the collected particulate matter and has been moved to position engaging the lid 61, is removed out of the filter unit mounting bay 39, and another filter unit 24 including a fresh filter 21 for collecting the particulate matter is mounted into the filter unit mounting bay 39. Then, the lid 61 is closed, and the filter 21 in the next filter unit 24, which takes the position engaging the sample gas supplying mechanism 36, is put into the practice of collecting the particulate matter as described above. The rotation of the turntable 37 and the operation of the sample gas supplying mechanism 36 are continued by a controller unit such as a microprocessor (not shown) to be operated alternately and automatically.

Note that the filter 21 included in the filter unit 24 removed from the filter unit mounting bay 39 is stored in a state not to contact the air.

The filter 21 can also be supplied with an impregnated tag or label material which can be carried in the reinforcing layer 23. This predetermined reference material is a material other than the SPM (a measuring target material) included in the atmosphere, and in a case where a quantitative analysis after measurement on a concentration of SPM with a β-ray is conducted with a PIXY analyzer, an element selected from the group consisting of Ti, Br, In, Pd and the like is adopted and a method is applied that the reinforcing layer 23 is impregnated into the element or woven thereinto with the element to cause the element to be carried therein in a predetermined amount. In a case where the quantitative analysis is conducted with an ion chromatographic instrument, a method is applied that the reinforcing layer 23 is impregnated with or woven thereinto with an element selected from the group consisting of Al, Ca, Cr, Cu, Fe, K, Mg, Mn, Na, Ni, Zn predetermined amount. The label material is preferably carried in the reinforcing layer 23 since the SPM collecting section 22 is made of fluororesin, and it is difficult for the label material to be carried in the SMP collecting section 22 with certainty, while the reinforcing layer 23 is a non-woven cloth low in hygroscopicity and made of one of polyethylene, polyethylene terepehtbalate, nylon, polyester and polyamide, and can carry the label material therein with certainty.

A measuring spot formed on the filter 21 by conducting sampling of air in the atmosphere for the predetermined time is illuminated with β-rays from the β-ray source to detect the β-rays transmitted through the tape filter 21 at the time with the β-ray detector. An intensity signal outputted from the β-ray detector is subjected to predetermined algorithm in the controller unit to obtain a total weight of dust, that is, the collected SPM and a concentration of collected SPM.

In order to quantitatively analyze SPM in the collected dust on individual components thereof quantitatively, a measuring spot on the filter 21 is analyzed, for example, with the PIXY analyzer to thereby enable individual components of SPM in the dust to be analyzed quantitatively. In this case, since a component (an element) other than measuring target components is carried as the label material in the reinforcing layer 23 of the filter 21 sensitivity correction in the PIXY analyzer is affected; thereby enabling measurement on a concentration of a desired measuring target component in the SPM with good precision and a high sensitivity.

Figure 12:
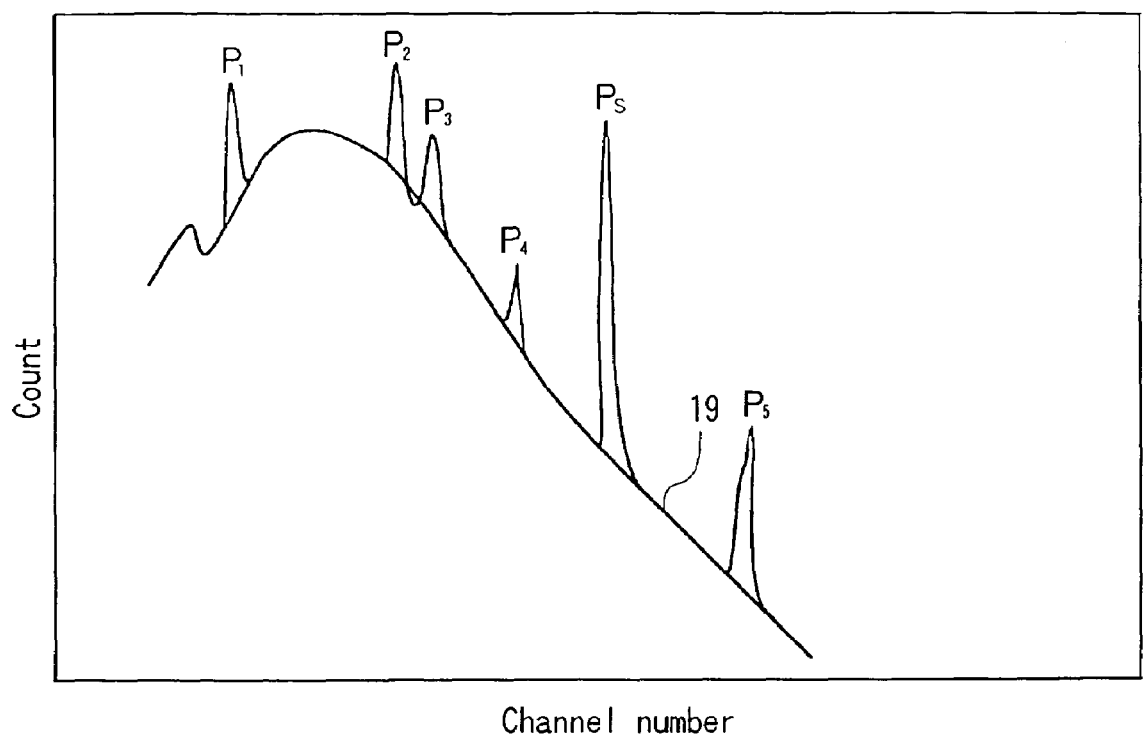
FIG. 12 is a graph showing the results of a quantitative analysis of SPM with a PIXY analyzer.

FIG. 12 shows a signal 19 obtained when a measuring spot portion is measured with the PIXY analyzer as a model, symbols $P_1$ to $P_5$ are peak signals corresponding to elements (components) such as Na, S, Cl, Ca and Fe included in the dust (SPM) collected in the measuring spot and a height of a peak is proportional to a concentration (an amount) of a corresponding element. The symbol P s is a peak signal corresponding to Ti carried as a label material in the reinforcing layer 23 of the filter 21. If a concentration (an amount) of titanium as the label material is, for example, 1 ppm, a peak height of the peak signal P s indicates 1 ppm; therefore, each correct concentration of the elements (amounts) can be determined with the peak height as a reference.

The sampler 34 has the following effects. A conventional sampler, which is operated by the batch for collecting the particulate matter on a filter with a cycle of at least 23 or 24 hours, must be stopped to change the filter after every cycle of an operation of collecting the particulate matter so that it is very time-consuming when plural cycles of operation for collecting particulate matter are carried out successively. On the contrary, the sampler 34 according to this embodiment is arranged, so that the turntable and the sample gas supplying mechanism are operated alternately and automatically, whereby the operation of collecting the particulate matter using the filter unit 24 (filter 21) and the change of the filter unit 24 can be carried out automatically and successively. Therefore, an operation such as changing the filter unit 24 is not required after every cycle of collection of particulate matter, and, as a result, the time and trouble for the collection of particulate matter can be shortened and saved.

Further, when the sampler 34 is arranged to be operated by, for example, a battery so as to be portable, the collection of particulate matter at, for example, a remote rural area, which is not supplied with electricity, can be carried out easily and successively.

Note that the invention is not limited to the embodiments described above, and various modifications may be available. For example, the filter is not limited to the shape of a circle in a plan view, but can take the shape of a ellipse or a polygon such as a rectangle in a plan view.

Further, the filter unit 24 is not limited to be formed with the individual components such as the base plate 25 and the retaining plate 26, but the filter unit 24 may be formed with pre-assembled components 25, 26 which are connected by a hinge (not shown) beforehand.

Still further, the gas S is not limited to atmosphere, but may be an exhaust gas such as an engine exhaust gas or a flue gas and a diluted exhaust gas which is generated by diluting the exhaust gas. In the latter cases, the objective particulate matter for analysis is the particulate matter contained in such exhaust gases.

Yet further, the time for passing the sample gas S through the filter 21 for collecting the particulate matter in the sample gas S is not limited to 24 hours, but can be 1 or a few hours or several days. The sampling time can be determined depending on the type or concentration of the sample gas.

Yet further, the number of the lid 26 attached to the cover 34 is not limited to one, but may be plural. In addition, the number of the mounting portion 25 engaged by a single lid 26 is not limited to one, but can be plural.

In the case of the sampler provided with a single lid 26 and a single mounting portion 25 which is engaged by the lid, when the filter 21 is intended to be removed after the sampler has been operated to collect particulate matter for several times successively without changing the filter 21, the turntable 23a is required to be rotated, then the filter 21 is taken out. However, such an inconvenience can be solved by attaching a plurality of lids 26 and mounting a plurality of mounting portions which are engaged by the plurality of lids 26. However, such an inconvenience can be solved by attaching a plurality of lids 34a and mounting a plurality of mounting portions which are engaged by the plural lid 34.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A particulate matter analyzer comprising:
   a collecting unit for collecting particulate matter in a sample gas of only a predetermined size range on a filter;
   a mass measuring unit for measuring mass of the particulate matter while on the filter; and
   a composition analyzing unit for analyzing composition of the particulate matter while on the filter, wherein the measurement of mass and analysis of composition are performed on the same collected particulate matter on the filter within the particulate matter analyzer.

2. The particulate matter analyzer of claim 1, wherein the composition analyzing unit is configured to analyze the composition of the particulate matter by irradiating a measuring spot formed on the filter with radioactive rays or electron beams.

3. The particulate matter analyzer of claim 2, wherein the collecting unit is configured to enable the sample gas to pass through the filter, thereby forming the measuring spot on the filter, and the filter is made of a material which substantially does not emit fluorescent x-rays.

4. The particulate matter analyzer of claim 3, wherein the filter has an antistatic electricity characteristic.

5. The particulate matter analyzer of claim 4, wherein the filter includes a porous layer made of a fluororesin, and a gas-permeable reinforcing layer which is provided on a surface of the porous layer.

6. The particulate matter analyzer of claim 5, wherein the reinforcing layer is made of a non-woven fabric which consists of any one or a plurality of materials selected from polyethylene, polyethylenetelephtalate, nylon, polyester, and polyamide.

7. The particulate matter analyzer of claim 6, wherein the filter includes a predetermined reference material other than a target material to be collected to enable a calibration of a particulate matter analyzer processing the collected target material on the filter.

8. The particulate matter analyzer of claim 3, wherein the unit for collecting particulate matter includes a filter holding mechanism with a plurality of individual filter holder units, and wherein the holder units are progressively and automatically position individual filters at a sample taking station which permits the sample gas to pass through selected filters.

9. The particulate matter analyzer of claim 1, wherein the mass measuring unit is configured to measure the mass of the particulate matter by using one of a beta-ray absorption method, a pressure loss method, and a light scattering method.

10. A system for collecting particulate matter in a fluid and analyzing mass of the particulate matter and its composition, comprising:
a collecting unit including a source of filter members for performing a plurality of sequential measurements and a sample fluid supplying unit for directing a predetermined amount of a sample to a filter member to separate particulate matter of a predetermined size range from the sample fluid;
a mass measuring unit for measuring the mass of the particulate matter while on the filter member;
a composition analyzing unit for analyzing the composition of the particulate matter while on the filter member;
a transporting unit for moving one of the plurality of filter members from the sample fluid supplying unit to respectively the mass measuring unit and the composition analyzing unit; and
a controller unit for automatically enabling the collecting unit, mass measuring unit, composition analyzing unit, and transporting unit, wherein a plurality of measurements with a plurality of filter members are carried out on the particulate matter over a predetermined time period.

11. The system of claim 10, wherein the source of filter members includes an elongated roll of filter material and a feeding reel unit which positions a predetermined length of filter material to operatively engage the sample fluid supplying unit.

12. The system of claim 10, wherein the source of filter members includes a filter holding mechanism which rotates a plurality of individual filter members to operatively engage the sample fluid supplying unit.

13. The system of claim 10, wherein the filter members have an antistatic characteristic.

14. The system of claim 10, wherein the filter members include a predetermined reference material other than a target material to be collected to enable a calibration of the composition analyzing unit.

15. The system of claim 10, wherein the mass measuring unit and the composition analyzing unit are within the same housing and measure the particulate matter at a same location within the housing.

16. The system of claim 10, wherein the filter members include a non-woven fabric low in hygroscopicity.

17. The system of claim 16, wherein the non-woven fabric consists of one of polyethylene, polyethylenetelephtalate, nylon, polyester, and polyamide.

18. The system of claim 10, wherein the filter members include a porous layer of a glass fiber, a reinforcing layer, and a predetermined reference material other than a target material to be collected to enable a reference comparison when the collected particulate matter on one of the filter members is subjected to an analysis to determine quantity of the target material.

19. A particulate matter analyzer comprising:
a collecting unit for collecting particulate matter in a sample gas including a size separator unit for supplying a predetermined size and smaller of particulate matter, an elongated filter member having an upper and a lower transporting unit for moving a predetermined length of the filter member to receive the particulate matter from the size separator unit;
a mass measuring unit for measuring mass of the particulate matter as deposited on the filter member;
a composition analyzing unit for analyzing composition of the particulate matter as deposited on the filter member; and
a controller unit for automatically enabling the collecting unit, the mass measuring unit, the composition analyzing unit, and the transporting unit to perform a plurality of measurements on a series of predetermined lengths of the filter member automatically over a predetermined time period without an operator.

20. The particulate matter analyzer of claim 19 wherein measurement of the mass and analysis of the composition is performed on the deposited particulate matter on the filter member when a predetermined length of the filter member is held stationary at one location by the transporting unit.

21. The particulate matter analyzer of claim 19 wherein the filter member includes, within each predetermined length of the filter member, a calibration reference material to enable a calibration of the composition analyzing unit.

22. The particulate matter analyzer of claim 19 wherein the mass measuring unit and the composition analyzing unit are within a single housing and measure the particulate matter at the same location on the filter member within the housing.

23. The particulate matter analyzer of claim 19 wherein the filter member has an antistatic electricity characteristic.

* * * * *